United States Patent
Leitao

(10) Patent No.: US 9,540,413 B2
(45) Date of Patent: Jan. 10, 2017

(54) METHOD FOR MONOFLUOROMETHYLATION OF ORGANIC SUBSTRATES TO PREPARE BIOLOGICALLY ACTIVE ORGANIC COMPOUNDS

(75) Inventor: Emilia Perpetua Tavares Leitao, Sao Marcos (PT)

(73) Assignee: HOVIONE INTER LIMITED, Lucerne (CH)

( * ) Notice: Subject to any disclaimer, the term of this patent is extended or adjusted under 35 U.S.C. 154(b) by 608 days.

(21) Appl. No.: 13/701,207

(22) PCT Filed: Jun. 1, 2011

(86) PCT No.: PCT/GB2011/000834
§ 371 (c)(1),
(2), (4) Date: Mar. 14, 2013

(87) PCT Pub. No.: WO2011/151624
PCT Pub. Date: Dec. 8, 2011

(65) Prior Publication Data
US 2013/0225844 A1 Aug. 29, 2013

(30) Foreign Application Priority Data
Jun. 1, 2010 (PT) .......................................... 105139

(51) Int. Cl.
*C07J 31/00* (2006.01)
(52) U.S. Cl.
CPC .................................... *C07J 31/006* (2013.01)
(58) Field of Classification Search
CPC ....................................................... C07J 31/006
USPC ........................................................ 552/610
See application file for complete search history.

(56) References Cited

U.S. PATENT DOCUMENTS

| 6,177,560 | B1* | 1/2001 | Heggie et al. | 540/116 |
| 9,290,446 | B2* | 3/2016 | Leitao | C07C 381/12 |
| 9,359,294 | B2* | 6/2016 | Leitao | C07C 381/12 |
| 2004/0043974 | A1* | 3/2004 | Albinson et al. | 514/179 |
| 2013/0072698 | A1* | 3/2013 | Leitao et al. | 549/484 |
| 2013/0274460 | A1* | 10/2013 | Leitao | 540/114 |

FOREIGN PATENT DOCUMENTS

| DE | 4330237 A1 | 3/1995 |
| WO | 0212266 A1 | 2/2002 |

OTHER PUBLICATIONS

Bohlmann et al., Abstract of DE4330237, Chemical Abstract Service, Retrieved on Sep. 29, 2011.
Peter Sykes, "A Guidebook to Mechanism in Organic Chemistry", Fifth Edition, 1988, pp. 228-230.
PCT International Search Report and Written Opinion, Application No. PCT/GB2011/000834 dated Oct. 10, 2011.
Bohlmann, et al., "1-(substituted methyl)- androsta-1, 4-diene-3, 17-diones as aromatase inhibitors", Chemical Abstracts Service, Columbus, Ohio, retrieved from STN, Database accession No. 1995:610611, DE4330237 abstract, web accessed Sep. 29, 2011.
Hu, et al., "Selective difluoromethylation and monofluoromethylation reactions", Chem. Commun., 2009, pp. 7465-7478.
Pool, "The Elusive Replacements for CFCs", Science, 1989, vol. 242, pp. 666-668.
Prakash, et al., "Direct Electrophili Monofluoromethylation", Organic Letters, 2008, vol. 10, No. 4, pp. 557-560.
Rossberg, et al., "Chlorinated Hydrocarbons", Ullmann's Encyclopedia of Industrial Chemistry, 2006, Wiley-VCH, Weinheim, pp. 1-186.
Sykes, "A Guidebook to Mechanism in Organic Chemistry", Fifth Edition, 1988, pp. 228-230.
Thayes, "Fabulous Fluorine", Chemical and Engineering News, Jun. 5, 2006, vol. 84, No. 23, pp. 15-24.
International Search Report, Application No. PCT/GB2011/000834 dated Oct. 10, 2011.
Written Opinion of the International Preliminary Examining Authority, Application No. PCT/GB2011/000834 dated Oct. 8, 2012.
Written Opinion of the International Searching Authority, Application No. PCT/GB2011/000834 dated Oct. 10, 2011.

* cited by examiner

*Primary Examiner* — Sabiha N Qazi
(74) *Attorney, Agent, or Firm* — MacMillan, Sobanski & Todd, LLC

(57) ABSTRACT

Described herein is a process for the preparation of monofluoromethylated organic biologically active compounds using monofluoromethylated reagents. Fluticasone Propionate and Fluticasone Furoate can be prepared using, for example, S-monofluoromethyl-S-phenyl-2,3,4,5-tetramethylphenylsulfonium tetrafluoroborate as monofluoromethylating reagent instead of bromofluoromethane.

12 Claims, 1 Drawing Sheet

R, $R_1$, $R_2$, $R_3$ = H, alkyl, aryl,

R4 = tetrafluoroborate, triflate, halogen

METHOD FOR MONOFLUOROMETHYLATION OF ORGANIC SUBSTRATES TO PREPARE BIOLOGICALLY ACTIVE ORGANIC COMPOUNDS

CROSS-REFERENCE TO RELATED APPLICATIONS

The present invention claims the benefit of the PCT/GB2011/000834 filed Jun. 1, 2011, which claims priority to Ser. No. PT/105139 filed Jun. 1, 2010.

BACKGROUND OF THE INVENTION

The carbon-fluorine bond is commonly found in pharmaceutical and agrochemical products, because it is generally metabolically stable and the fluorine atom acts as a bioisostere of the hydrogen atom (Ann M. Thayer "Fabulous Fluorine" Chemical and Engineering News, June 5, 2006, Volume 84, pp. 15-24). Nowadays around 20% of all pharmaceutical compounds and 30-40% of agrochemicals on the market contain fluorine. Fluorination and fluoroalkylation are the two major synthetic methods to prepare selectively fluorinated organic compounds. The monofluoromethylation (selective introduction of a $CH_2F$ group into the organic molecule) is less studied than fluorination.

The exploration of di- and monofluoromethylated compounds as organic biologically active compounds has emerged recently. As a result, a variety of structurally diverse $CH_2F$-containing drugs have been developed, such as: Afloqualone, Fluticasone Propionate (Jinbo Hu; Wei Zhang; Fei wang; Chem. Commum., 2009, 7465-7478), the anaesthetic Sevoflurane, Fluticasone Furoate.

The efficient and selective incorporation of monofluoromethylated moieties into the organic molecule is beneficial for the synthesis of the target molecule. The process is usually carried out directly using $CH_2FBr$ or indirectly, using $CH_2BrI$ or $CH_2ClI$, among others. These compounds are known as hydrochlorofluorocarbons or freons (HCFCs), which is a subclass of chlorofluorocarbons (CFCs).

Every permutation of fluorine, chlorine, and hydrogen on the methane and ethane core has been examined and most have been commercialized. Furthermore, many examples containing bromine are known for higher numbers of carbon as well as related compounds. The use of this class of compounds includes refrigerants, blowing agents, propellants in medicinal applications, and degreasing solvents (M. Rossberg et al. "Chlorinated Hydrocarbons" in Ullmann's Encyclopedia of Industrial Chemistry 2006, Wiley-VCH, Weinheim).

Unfortunately, due to their high stability, CFCs do not decompose in the lower atmosphere as many industrial chemicals do. In fact they are accumulating and eventually rise to the stratosphere. Ultraviolet radiation in the stratosphere breaks the CFCs apart, and the released chlorine atoms destroy the ozone layer. For this reason, the manufacture of such compounds is being phased out according to the Montreal Protocol (Pool, R. 1989. The elusive replacements for CFCs. Science 242: 666). Under the Montreal Protocol, it was agreed to start reducing their consumption and production in 2015.

Recently, Prakash et al. reported a new electrophilic monofluoromethylation reagent for direct transfer of +$CH_2F$ (S-monofluoromethyl-S-phenyl-2,3,4,5-tetramethylphenylsulfonium tetrafluoroborate) to certain nucleophiles such as sulfonic acids, tertiary amines, imidazole derivatives, and phosphine (G. K. Surya Prakash; Istvan Ledneczki; Sujith Chacko; George A. (Olah; Org. Lett., vol. 10, No.4, 2008).

DETAILED DESCRIPTION OF THE INVENTION

Figure 1:
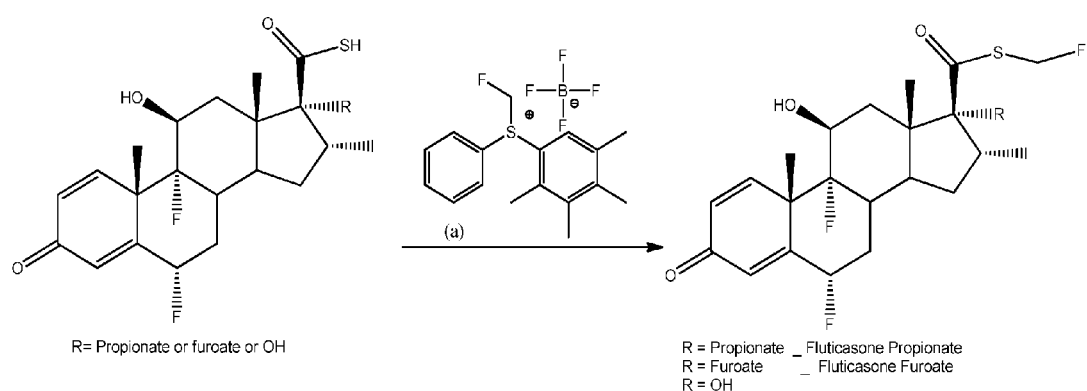
FIG. 1. Schematic illustration of synthesis of fluticasone propionate and fluticasone furoate.
Figure 2:
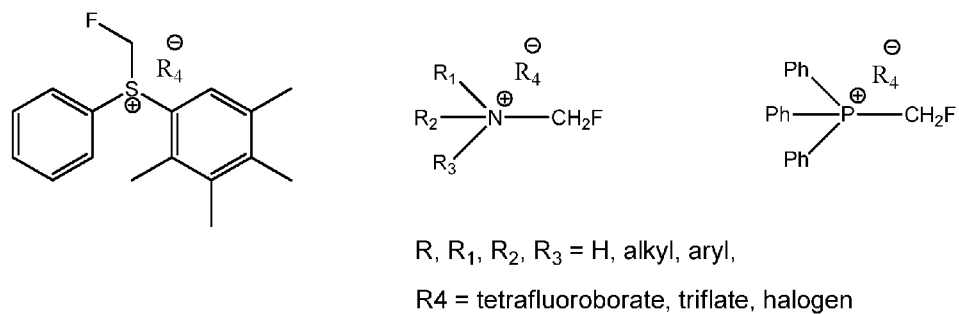
FIG. 2. Schematic illustration showing monofluoromethylating reagents.

We have now devised a way of introducing the —$CH_2F$ group onto a sulphur atom, in particular a thiol (S—H) group, and in this way are able to avoid the use of reagents that deplete the ozone layer. Hence, for example, S-monofluoromethyl-S-phenyl-2,3,4,5-tetramethylphenylsulfonium tetrafluoroborate (a) or triflate can be used to prepare Fluticasone Propionate and Fluticasone Furoate as shown in FIG. 1.

This method can also be used for the preparation of monofluoromethylated intermediate compounds, such as quaternary amines, tetrafluoroborate salts, monofluoromethylated imidazoles tetrafluoroborate salts and sulfonic salts and in turn each of these compounds can also be used to prepare Fluticasone Propionate and Fluticasone Furoate or other organic biologically active compounds containing a $CH_2F$ group, such as Afloqualone and Sevoflurane.

According to one aspect of the present invention, there is provided a method of preparing an organic biologically active compound containing a "$CH_2F$" moiety, which method comprises the use of a monofluoromethylating reagent characterized by one of the following formulas I, II and III:

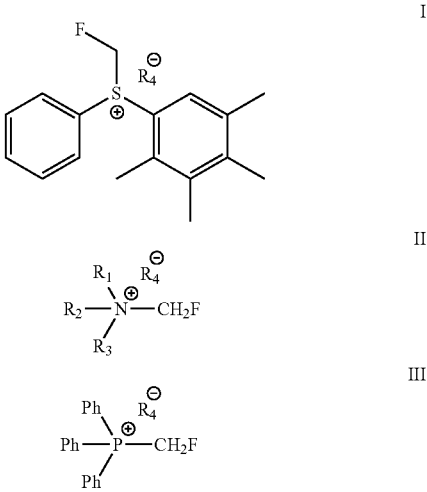

wherein:
$R_1$, $R_2$, $R_3$ is independently selected from the group consisting of hydrogen, alkyl or aryl; and
$R_4$ is an anion suitable to form a salt of the reagents presented above, selected from the group consisting of tetrafluoroborate, triflate and halogen.

In a preferred aspect, the method of the invention is used to provide a compound of Formula IV, such as fluticasone furoate or fluticasone propionate.

In another aspect the invention provides the use of a monofluoromethylating reagent in the preparation of an organic biologically active compound containing a "CH$_2$F" moiety.

Suitably, the organic biologically active compound may be obtained by monofluoromethylation of a suitable organic substrate, which is typically a precursor compound. The organic substrate may be an inmmediate or direct precursor compound to the organic biologically active compound, or may be an earlier intermediate compound at any appropriate stage in the synthetic process. The stage of monofluoromethylation in the synthetic process will generally be determined by the active compound in question, as will be clear to those skilled in the art.

By "organic biologically active compound" we mean an organic compound which is of medical or therapeutic use in the broadest sense. Typically, the compounds are pharmaceutically active compounds. Preferred compounds include steroidal compounds, particularly glucocorticoid compounds, especially glucocorticoids such as fluticasone.

Preferably, the organic substrate or precursor compound comprises a thiol group (S—H). Preferred compounds include steroidal compounds, particularly those comprising a thiol group. Glucocorticoid compounds are particularly preferred, especially precursors to pharmaceutically active glucocorticoids such as fluticasone.

In addition, if desired, the organic substrate or precursor compound may comprise one or more hydroxyl (—OH) groups. We have found that, surprisingly, compounds having one or more hydroxyl groups can be satisfactorily monofluoromethylated (especially at a thiol (S—H) group) without needing to protect the hydroxyl group (for example, at the C$_{11}$ position in a steroidal compound).

Thus, in a preferred aspect, there is provided a method of preparing an organic biologically active compound containing a "CH$_2$F" moiety, which method comprises the step of monofluoromethylating an organic substrate or precursor compound for the said active compound, which substrate or precursor comprises a thiol (S—H) group, using a monofluoromethylating reagent characterised by one of the following formulas I, II and III:

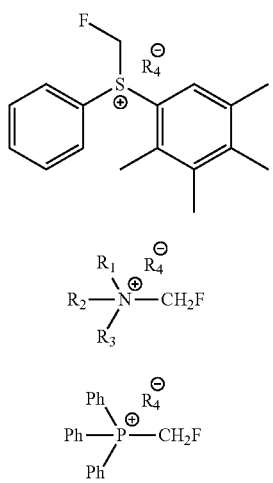

wherein:
R$_1$, R$_2$, R$_3$ is independently selected from the group consisting of hydrogen, alkyl or aryl; and R$_4$ is an anion suitable to form a salt of the reagents presented above, selected from the group consisting of tetrafluoroborate, triflate and halogen.

Organic biologically active compounds can be obtained by monofluoromethylation of organic substrates with the following monofluoromethylating reagents:

In the compound of formula II, "alkyl" is preferably a primary alkyl with from one to five carbon atoms (C$_1$-C$_5$), with methyl particularly preferred. However, branched alkyl may be used if desired, and may optionally be substituted. "Aryl" is preferably phenyl or substituted phenyl.

In terms of the amounts of substrate and monofluoromethylating reagent used, preferably from 0.9 to 2 mole equivalents of monofluoromethylating reagent is used per mole of organic substrate (or precursor compound). A ratio of from about 1:1 to 1:1.2 (substrate:reagent) is particularly suitable, particularly when making fluticasone derivatives or similar steroidal compounds.

The temperature at which the reaction between substrate and monofluoromethylating reagent is carried out is suitably from −15° C. to 50° C. For many reactions, room temperature (20-25° C.) is suitable

EXAMPLES

The following reagents are given as examples but do not limit the scope of the invention:

S-monofluoromethyl-S-phenyl-2,3,4,5-tetramethylphenylsulfonium tetrafluoroborate, S-monofluoromethyl-S-phenyl-2,3,4,5-tetramethylphenylsulfonium triflate, salts thereof.

P-monofluoromethyltriphenylphosphonium tetrafluoroborate, P-monofluoromethyltriphenylphosphonium triflate and salts thereof.

N-(monofluoromethyl) triethylammonium tetrafluoroborate, N-(monofluoromethyl) triethylammonium triflate and salts thereof.

N-(monofluoromethyl)-N-phenyl-dimethylammonium tetrafluoroborate, N-(monofluoromethyl)-N-phenyl-dimethylammonium triflate and salts thereof.

Example 1

Preparation of fluticasone 17-propionate with S-monofluoromethyl-S-phenyl-2,3,4,5-tetramethylphenylsulfonium triflate in dichloromethane:

2 g (4.27 mmol) of 17-propionate carbothioic acid (full name: 6α,9α-Difluoro-11β-hydroxy,16α-methyl-3-oxo-17α-(propionyloxy) androsta-1,4-diene-17β-carbothioic acid) was dissolved in 49 ml of dichloromethane. 0.756 g (0.54 eq) of cesium carbonate and 1.928 g (1.06 eq) of S-monofluoromethyl-S-phenyl-2,3,4,5-tetramethylphenylsulfonium triflate were added. The resulting mixture was stirred at room temperature until the reaction is complete. The mixture was added to 250 ml of heptane. The dichloromethane was removed by distillation. The solid was isolated by filtration, washed with heptane and dried under vacuum at a temperature below 35° C. The solid was recrystallized from a mixture of acetone and water. The salts are purged during this recrystallization.

Example 2

Preparation of fluticasone 17-propionate with S-monofluoromethyl-S-phenyl-2,3,4,5-tetramethylphenylsulfonium triflate in acetonitrile:

5 g (10 7 mmol) of 17-propionate carbothioic acid was suspended in 50 ml of acetonitrile. 3.39 g (1 eq) of cesium carbonate was added. The resulting suspension was stirred for 5 minutes at room temperature. 4.54 g (1.0 eq) of S-monofluoromethyl-S-phenyl-2,3,4,5-tetramethylphenyl-sulfonium triflate was added. The suspension was stirred at room temperature until the reaction is complete. The solid was isolated by filtration, washed with 10 ml of acetonitrile and then with 10 ml of heptane at 5° C. The solid was dried under vacuum at a temperature below 35° C. The solid was recrystallized from a mixture of acetone and water. The salts are purged during this recrystallization.

Example 3

Preparation of fluticasone 17-propionate with S-monofluoromethyl-S-phenyl-2,3,4,5-tetramethylphenylsulfonium tetrafluoroborate in dichloromethane:

5 g (10 7 mmol) of 17-propionate carbothioic acid was dissolved in 50 ml of dichloromethane. 3.39 g (1 eq) of cesium carbonate was added and the solution turned into a suspension. The suspension was stirred for 40 minutes at room temperature. 4.57 g (1.18 eq) of S-monofluoromethyl-S-phenyl-2,3,4,5-tetramethylphenyl sulfonium tetrafluoroborate was added. The mixture was stirred at room temperature until the reaction is complete. The solid was isolated by filtration, washed with 10 ml of dichloromethane and washed twice with 10 ml of heptane. The solid was dried under vacuum at a temperature below 35° C. The solid was recrystallized from a mixture of acetone and water. The salts are purged during this recrystallization.

Example 4

Preparation of fluticasone 17-propionate with S-monofluoromethyl-S-phenyl-2,3,4,5-tetramethylphenylsulfonium tetrafluoroborate in acetonitrile:

5 g (10 7 mmol) of 17-propionate carbothioic acid was suspended in 50 ml of acetonitrile. 3.39 g (1 eq) of cesium carbonate was added. The resulting suspension was stirred for 5 minutes at room temperature. 3.9 g (1 eq) of S-monofluoromethyl-S-phenyl-2,3,4,5-tetramethylphenylsulfonium tetrafluoroborate was added. The mixture was stirred at room until the reaction is complete. The solid was isolated by filtration, washed with 10 ml of acetonitrile at 5° C. and dried under vacuum at a temperature below 35° C. The solid was recrystallized from a mixture of acetone and water. The salts are purged during this recrystallization.

Example 5

Preparation of fluticasone 17-propionate with N-(monofluoromethyl) triethyl ammonium triflate in acetonitrile:

0.5 g (1.07 mmol) of 17-propionate carbothioic acid was suspended in 5 ml of acetonitrile. 0.218 g (0.63 eq) of cesium carbonate and 0.604 g (2.13 eq) of N-(monofluoromethyl) triethylammonium tetrafluoroborate were added. The mixture was stirred at room temperature until the reaction is complete. The solid was isolated by filtration, washed with 0.5 ml of acetonitrile and then with 1 ml of water. The solid was dried under vacuum at a temperature below 35° C.

Example 6

Preparation of fluticasone 17-propionate with N-(monofluoromethyl)-N-phenyl-dimethylammonium triflate in acetonitrile:

0.5 g (1.07 mmol) of 17-propionate carbothioic acid was suspended in 5 ml of acetonitrile. 0.218 g (0.63 eq) of cesium carbonate was added. The resulting suspension was stirred for 30 minutes prior to the addition of 0.5 g (1.5 eq) of N-(monofluoromethyl)-N-phenyl-dimethylammonium triflate. The resulting mixture was stirred at room temperature until the reaction is complete. The solid was isolated by filtration, washed with 5 ml of cold acetonitrile and dried at a temperature below 35° C. The solid was suspended in water to remove the salts and then dried.

Example 7

Preparation of fluticasone 17-propionate with P-monofluoromethyltriphenylphosphonium tetrafluoroborate in acetonitrile:

1 g (2.13 mmol) of 17-propionate carbothioic acid was suspended in 12 ml of acetonitrile. 0.45 g (0.65 eq) of cesium carbonate and 1.4 g (1.7 eq) of P-monofluoromethyltriphenylphosphonium tetrafluoroborate were added. The mixture was stirred at room temperature until the reaction is complete. The solid was isolated by filtration, washed twice with 3 ml of acetonitrile previously cooled to 5° C. and then with 3 ml of water. The solid was dried under vacuum at a temperature below 35° C.

Example 8

Preparation of fluticasone 17-furoate with S-monofluoromethyl-S-phenyl-2,3,4,5-tetramethylphenylsulfonium triflate in acetonitrile:

2.5 g (4.93 mmol) of carbothioic acid 17-furoate (full name: 6α,9α-Difluoro-17α-[(2-furanylcarbonyl)oxy]-11β-hydroxy-16α-methyl-3-oxo-androsta-1,4-diene-17β-carbothioic acid) was suspended in 10 ml of acetonitrile. 1.04 g (0.65 eq) of cesium carbonate and 3.0 g (1.43 eq) of S-monofluoromethyl-S-phenyl-2,3,4,5-tetramethylphenylsulfonium triflate were added. The resulting suspension was stirred at room temperature until the reaction is complete. The solid was isolated by filtration, washed twice with 2.5 ml of acetonitrile previously cooled to 5° C. and dried under vacuum at a temperature below 35° C. The solid is recrystallized from a mixture of acetone and water. The salts are purged during this recrystallization.

Example 9

Preparation of fluticasone 17-furoate with S-monofluoromethyl-S-phenyl-2,3,4,5-tetramethylphenylsulfonium tetrafluoroborate in acetonitrile:

2.5 g (4.93 mmol) of carbothioic acid 17-furoate was suspended in 10 ml of acetonitrile. 1.04 g (0.65 eq) of cesium carbonate and 2.1 g (1.18 eq) of S-monofluoromethyl-S-phenyl-2,3,4,5-tetramethylphenylsulfonium tetrafluoroborate were added. The resulting suspension was stirred for 1 hour at room temperature. The solid was isolated by filtration, washed twice with 2.5 ml of acetonitrile previously cooled to 5° C. The solid was dried under vacuum at a temperature below 35° C. The solid is recrystallized from a mixture of acetone and water. The salts are purged during this recrystallization.

Example 10

Preparation of fluticasone 17-furoate with N-(monofluoromethyl)-N-phenyl-dimethylammonium triflate in acetonitrile:

0.5 g (0.987 mmol) of carbothioic acid 17-furoate was suspended in 5 ml of acetonitrile. 0.208 g (0.65 eq) of cesium carbonate and 0.4 g (1.34 eq) of N-(monofluoromethyl)-N-phenyl-dimethylammonium triflate were added. The resulting suspension was stirred for 4 hour at room temperature. The solid was isolated by filtration, washed twice with 1 ml of acetonitrile previously cooled to 5° C. and then with 1 ml of deionised water. The solid was dried under vacuum at a temperature below 35° C. The solid is recrystallized from a mixture of acetone and water. The salts are purged during this recrystallization.

It is evident to one skilled in the art that this invention is not limited to the foregoing examples, and that can be embodied in other specific forms without departing from the scope of the invention. Thus, the examples should be considered as illustrative and not restrictive, reference being made to the claims, and that all changes which come within the meaning and range of equivalency of claims be embraced therein.

The invention claimed is:

1. A method of preparing a pharmaceutically active compound containing a "CH$_2$F" moiety on a sulphur atom, which method comprises the use of a monofluoromethylating reagent characterized by formula I:

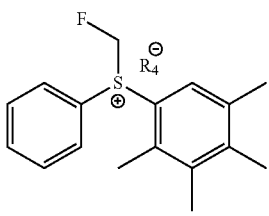

wherein:
R$_4$ is an anion suitable to form a salt of the reagent presented above, selected from the group consisting of tetrafluoroborate, triflate and halogen;
by reacting with a compound of formula A:

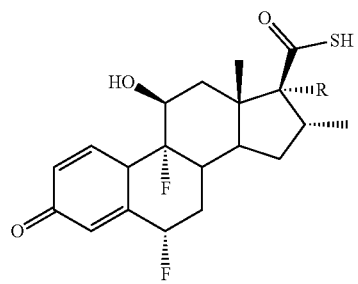

wherein R is selected from the group consisting of hydroxyl, furoate and propionate;
wherein the pharmaceutically active is a compound of Formula IV:

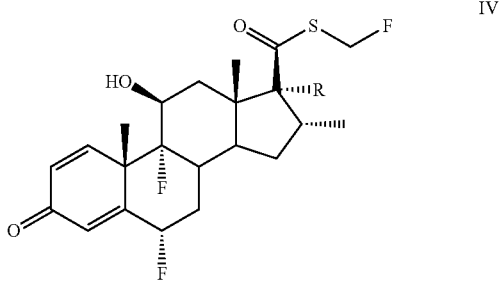

wherein R is selected from the group consisting of hydroxyl, furoate and propionate.

2. A method according to claim 1, wherein R$_4$ is triflate or tetrafluoroborate.

3. A method according to claim 1, wherein R is propionate or furoate.

4. A method according to claim 1, wherein the compound of formula IV is prepared using S-monofluoromethyl-S-phenyl-2,3,4,5-tetramethylphenylsulfonium tetrafluoroborate salt as monofluoromethylating reagent.

5. A method according to claim 1, wherein the compound of formula IV is prepared using S-monofluoromethyl-S-phenyl-2,3,4,5-tetramethylphenylsulfonium triflate salt as monofluoromethylating reagent.

6. A method according to claim 1, wherein the preparation of the pharmaceutically active compound comprises an organic solvent.

7. A method according to claim 6, wherein the solvent is selected from the group consisting of acetonitrile, heptane, hexane, cyclohexane, methyl tert-butyl ether (MTBE), dimethylformamide (DMF), toluene, 1,2-dichloromethane, α,α,α-trifluorotoluene, tetrahydrofurane (THF), methyl-THF, 1,2-dimethoxyethane and mixtures thereof.

8. A method according to claim 1, wherein the preparation of the pharmaceutically active compound comprises use of a base.

9. A method according to claim 8, wherein the base is a weak base.

10. A method according to claim 8, wherein the base is an inorganic carbonate.

11. A method according to claim 10, wherein the base is selected from the group consisting of cesium carbonate, sodium carbonate and potassium carbonate, and mixtures thereof.

12. A method according to claim 11, wherein the base is cesium carbonate.

* * * * *